United States Patent
Filhol

(10) Patent No.: US 6,575,748 B1
(45) Date of Patent: Jun. 10, 2003

(54) DENTAL TOOL

(76) Inventor: Stuart Julian Filhol, Castlefreke, County Cork (IE)

(*) Notice: Subject to any disclaimer, the term of this patent is extended or adjusted under 35 U.S.C. 154(b) by 0 days.

(21) Appl. No.: 09/830,656

(22) PCT Filed: Oct. 27, 1999

(86) PCT No.: PCT/EP99/08117
§ 371 (c)(1),
(2), (4) Date: Aug. 2, 2001

(87) PCT Pub. No.: WO00/25698
PCT Pub. Date: May 11, 2000

(30) Foreign Application Priority Data

| Oct. 30, 1998 | (GB) | ................................ 9823814 |
| Nov. 17, 1998 | (EP) | ................................ 98309388 |
| Mar. 17, 1999 | (GB) | ................................ 9906163 |

(51) Int. Cl.[7] .................................................. A61C 5/02
(52) U.S. Cl. ..................................................... 433/102
(58) Field of Search .......................... 433/81, 102, 224

(56) References Cited

U.S. PATENT DOCUMENTS

| 1,771,182 A | * | 7/1930 | Lentulo | ........................ 433/164 |
| 1,969,808 A | * | 8/1934 | Lentulo | ........................ 433/164 |
| 3,906,636 A | * | 9/1975 | Rainey et al. | ............... 433/102 |
| 4,536,156 A | * | 8/1985 | Cattin | .......................... 433/102 |
| 4,904,185 A | * | 2/1990 | McSpadden | ................. 433/164 |
| 5,632,620 A | * | 5/1997 | Musikant et al. | ............ 433/102 |

FOREIGN PATENT DOCUMENTS

| DE | 837146 | 4/1952 |
| DE | 3734303 | 4/1989 |
| FR | 901370 | 7/1945 |
| FR | 2547718 | 12/1984 |

* cited by examiner

Primary Examiner—John J. Wilson
(74) Attorney, Agent, or Firm—Dickstein, Shapiro, Morin & Oshinsky, L.L.P.

(57) ABSTRACT

A dental root canal file (1) has a drilling end (5) and a shank (7) formed of a hollow, substantially closed, helix (16), and openings (14) are defined between the adjacent windings (8a, 8b, 8c) by spacers (13).

20 Claims, 2 Drawing Sheets

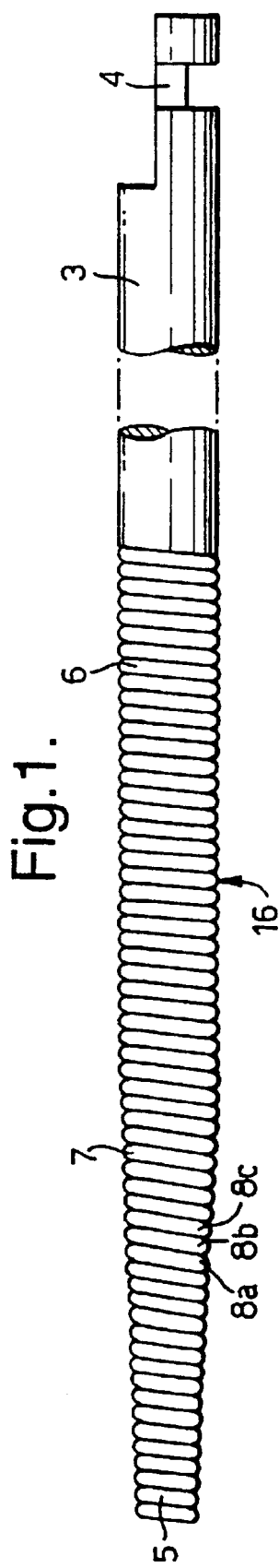
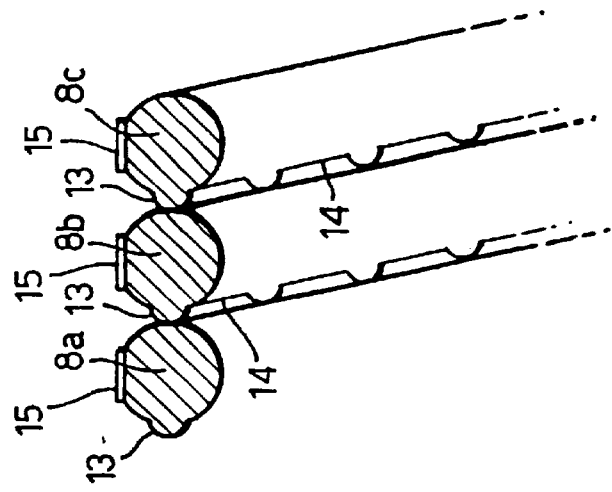
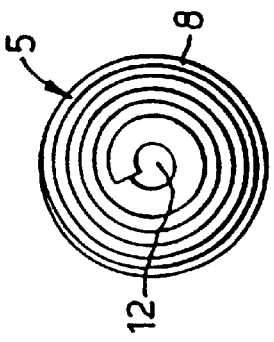

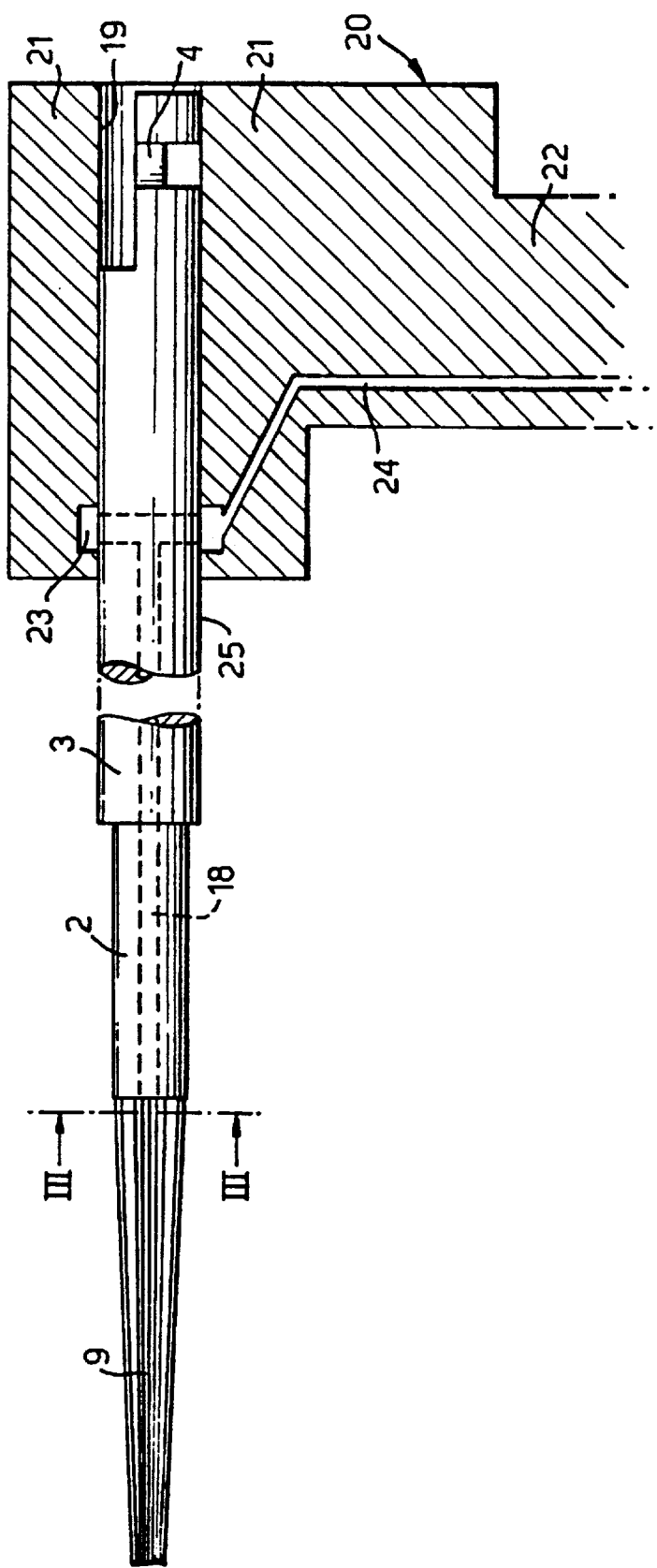
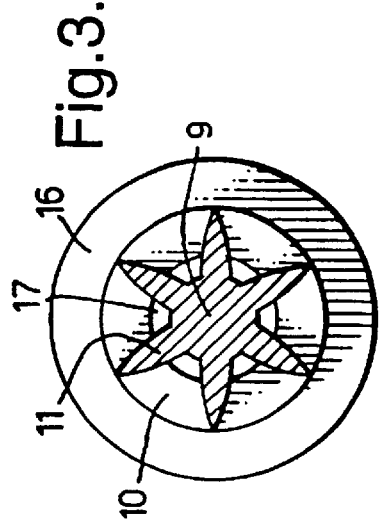
Fig.2.
Fig.3.

DENTAL TOOL

This invention relates to a dental tool for drilling (including cleaning) the dental root canal.

The dental root canal is an elongated passage which is narrow (typically being not more than 2 mm wide at its widest part) and is curved. In particular, it tends to be curved near its tip, which is where it is narrowest.

It is necessary to be able to clean debris out of the passage and it is also necessary to be able to prepare the passage, by drilling, for reception of a filling. Typically the prepared passage has an included angle in the range 10 to 15° at its mouth end and of less than 2°, for instance around 1°, at its tip.

The root canal at present is generally cleaned and drilled using a solid file formed by twisting a square or triangular rod. The solid twisted rod has to be sufficiently thin and narrow that it can penetrate the canal. It has to withstand the repeated flexing that is caused by the curvature of the canal as the rod is rotated within it. Accordingly there is a risk of breakage.

In practice the file is usually rotated by hand, relatively slowly, and this minimises the problems of flexing and the risk of breakage. When the file is operated by a drill, for instance at 300 to 500 rpm, this causes very rapid flexing. This increases the risk of breakage of the file within the canal.

It is known to use an open helix, optionally coated with abrasive, as a paste filler or pulp extractor, for instance from DE-C-837146 and FR-B-901370, but these are not suitable for preparing the passage by drilling.

It is known from DE-A-37343003 to use a drill having a drilling head at the tip of a coil spring of uniform diameter, but this arrangement does not give effective drilling and cleaning, especially along the entire length, including in the narrow tip, of the canal and does not provide for removal of the debris.

In FR-A-2547718 the use of a tapered helix is described, with the helix surrounding a metallic filament. In theory this arrangement may be capable of giving some drilling and cleaning along the length of the canal but in practice it will be relatively ineffective because it does not provide any means for removing the debris from the canal. Thus if the drill is rotated so as to tighten the helix on to itself, rotation of the drill will merely force the debris further down into the canal. If the drill is rotated so as to loosen the helix, the helix is likely to become unwound and enlarged and will jamb in the root canal.

The purpose of the invention is to provide a root canal file by which it is possible to clean and drill the extremeties of the root canal and which will facilitate removal of debris from within the canal, and in particular to provide such a file which will achieve this object with minimum risk of breakage even when it is being rotated by a dental drill at, for instance, 500 rpm.

A dental root canal file according to the invention has a drilling end and a holder end interconnected by a shank. The drilling end and the shank have a maximum diameter of not more than 2 mm and are formed of a single hollow helix or are formed of two or more hollow helices which are co-wound and are interconnected substantially in end-to-end relationship. The or each helix is a substantially closed hollow winding which can flex during drilling rotation and has an external surface which is abrasive to dental root canal material. Adjacent windings of the helix, or of at least one of the helixes, carry spacers whereby adjacent windings are in contact with each other but define openings between the windings.

The file can be fitted onto a stub of a conventional rotatable dental tool holder which can be mounted for rotation in conventional manner on a dental drill.

There is normally at least one internal lengthwise passage along the drilling end and the shank towards the holder end for the transfer of material towards the holder end or towards the drilling end. The holder into which the file can be fitted may include means for transferring material from or to this passage. For instance the holder may include means for applying suction to the passage so as to suck debris out of the canal or it may include means for forcing a fluid from the holder along the passage towards the tip, for irrigating the canal.

The invention is illustrated in the accompanying drawings in which

FIG. 1 is a perspective view of a file according to the invention mounted on a dental tool holder;

FIG. 2 is a similar view of a suitable holder;

FIG. 3 is a cross-section on the line III—III in FIG. 2;

FIG. 4 is an end view of the tip of the file;

FIG. 5 is a longitudinal cross-section through a portion of the file showing details of the individual windings.

The file 1 is mounted on a stub 2 of a dental tool holder 3 having a conventional latch configuration 4 for fitting within a dental drill.

The file has a drilling end 5, a holder end 6 and a shank 7 interconnecting the drilling end 5 and the holder end 6. The holder end 6 fits over the stub 2 of the holder.

The file can have a uniform diameter along its shank to its drilling end, but preferably is tapered to a minimum diameter at the drilling end. Typically this drilling end has a diameter of less than 0.5 mm and usually less than 0.4 mm, for instance around 0.1 to 0.3 mm.

The shank therefore usually has a maximum diameter (at the holder end) which is greater than the diameter at the drilling end, for instance in being 1.3 to 3 times, often around 1.5 to 2 times the diameter of the drilling end. The maximum diameter of the shank is usually above 0.3 mm and normally above 0.5 mm. In some instances it can be as much as 2 mm but is usually less than 1.5 mm, and often less than 1 mm. Typically therefore no part of the holder end and shank has a diameter less than about 0.3 mm and no part has a diameter greater than about 1 or 1.5 mm.

In the embodiment shown in the drawings, the file is formed from a single hollow helix 16 which is a substantially closed hollow winding. By saying it is substantially closed, we mean that adjacent windings (for instance as shown at 8a, 8b and 8c) are substantially in contact with one another when the helix is not in use. As a result, the length of the helix remains substantially constant even if axial pressure is applied. Thus, the axial length is preferably unchanged as a result of the application of axial compression or, if there is any reduction in length, the amount is very small, for instance not more than 10% and usually not more than 5%. It is particularly preferred that axial compression does not reduce the length of the drilling end. Generally adjacent windings are in tight contact with each other (when not in use).

The twist of the helix is normally counter to the direction of rotation of the dental tool holder during use, and in particular the twist of the helix is usually counter clockwise since the dental tool holder normally rotates clockwise. Because the twist of the helix is counter to the direction of rotation, the diameter of the helix will reduce slightly, due to tightening of the winding, during rotational use. The dimensions quoted above are of the helix in the relaxed state.

The helix is a hollow helix in that it is wound out of very fine wire, for instance having a diameter of 1 to 4, preferably about 2 to 4, thousandths of an inch (25–100 μm, preferably 50–100 μm).

Typically the pitch of the helix is 1 to 1.5 times, typically 1 to 1.2 times the diameter of the wire and from 1/5 to 1/25 the diameter of the shank. The drilling end typically has a diameter of 3 to 10 times, typically around 5 to 6 times, the diameter of the wire. The shank typically has a diameter of 15 to 40 times, often around 20 to 30 times, the diameter of the wire. The drilling end and the shank typically has a length of 10 to 20 mm.

As shown in FIG. 4, the drilling tip 5 of the file may be terminated by the wire 8 being wound into a tapered coil which is open at its centre 12.

The file is normally formed of a single helix but if desired it may be formed of two or more helices which are interconnected in substantially end to end relationship, for instance by being mounted on a holder such as the web 9 described below. The interconnection should be such that the file can still flex and function as a file when it is rotated by the dental drill. All the helices will normally be co-wound, i.e. wound in the same direction.

The wire can be of any suitable material such as carbon steel, stainless steel or titanium or an alloy, for instance a nickel titanium alloy such as 30% nickel 70% titanium.

The helix is hollow, as in a spring, and the drilling end is preferably open. Preferably the file defines an internal lengthwise passage for transfer of debris along the drill from the drilling end towards the holder end. In order to control the flexing of the drilling end and the shank it is often preferable to provide a flexible web 9 in the hollow core of the helix in order to support the individual windings of the helix and to reduce the risk of distortion during flexing. This web 9 can be an extension of the stub 2 or may be a separate element inserted into the file. The web 9 preferably defines, with the helix, one or more elongated passages 10 for the transfer of material along the length of the file. For example, as shown in FIG. 3, the web 9 may have a plurality of radially extending arms or ribs 11 for supporting the helix, which is shown diagrammatically in FIG. 3 at 16. The web may be of rubber or other flexible material which is capable of flexing rapidly while supporting the helix.

Although the helix is formed of one or more substantially closed windings, it is desirable that the helix should, during use, allow the passage of debris into the hollow core, generally over part or all of the length of the drilling end. This necessitates that there should be adequate openings between the individual windings during use.

In order to facilitate the passage of debris into the hollow core, adjacent windings of the or each helix which form the drilling end (and preferably also the shank) may carry lengthwise spacers 13 so that the adjacent windings 8a, 8b and 8c are in contact through the spacers 13 that define openings 14 between the windings. The spacers can have any construction which allows for the adjacent windings to be in contact with one another through the spacers while still defining spaces between the windings. A preferred form of spacer 13 is provided merely by embossing adjacent faces of the windings, since the embossed (recessed) faces will then define openings 14 and the non-embossed parts will define the spacers 13. Although it is preferred to form the spacers 13 by cutting or embossing the wire from which the helix is made (usually before forming the helix) it is also possible to apply spacers 13 to preformed wire. The dimensions of the openings 14 and the spacers 13 can be very small, for instance no greater than the diameter of the wire and often considerably less, for instance down to 1/10th of the diameter of the wire.

Although the windings 8a, 8b, 8c are normally in tight contact with each other when not in use, during use the helix normally is flexed due to its rotation within a root canal which is not rectilinear but is instead curved. This flexing may, in some embodiments, provide sufficient openings during use to allow adequate passage of debris or irrigation fluid through the openings. Accordingly, in another embodiment, the drill is as defined and described throughout this specification except that there is no deliberate provision of the lengthwise spacers. Generally, however, this gives inferior results.

The external surfaces of the windings must be abrasive to dental root canal material, at least over part of their length. Generally the windings are shaped so as to provide outwardly facing abrasion surfaces 15. For instance abrasive material may be bonded to the outwardly facing surface of the helix 16 or the outwardly facing surface of each winding may be shaped so as to improve its abrasiveness with respect to the material which is in and surrounds the dental root canal. The helix can, for instance, be formed of a wire which has been indented prior to forming into a helix so as to define the spacer 13 and/or the abrasion surfaces 15.

The file can be caused to rotate by manual rotation or, more usually, by drill rotation, for instance at several hundred rpm e.g. 300 to 500 rpm. Because the helix is thin and flexible, it can rotate within the canal while flexing to the configuration of the canal and can be used to remove debris and to reshape the canal.

In practice, the file is mounted in a conventional dental hand piece head, which may be constructed either for manual rotation or for drill rotation.

It is desirable that the holder for the file should include means for transferring material from or to the hollow core.

For instance, if significant amounts of debris accumulate in the hollow core there may be a risk that they will be forced back into the root canal or into the bone. It is therefore desirable to be able to suck the debris from the core. Also, it is desirable to be able to monitor the nature of the debris which is being drilled by the file, for instance so as to observe when the tip of the file passes from the tooth to the bone.

Also, it can be desirable to irrigate and disinfect the root canal by forcing air or a liquid into the root canal.

It is therefore preferred that the holder should include a passage which inter-connects with the hollow core and by which debris can be drawn out of the hollow core away from the drilling tip, and/or gas or liquid can be forced into the hollow core and outwardly into the root canal.

A suitable arrangement is illustrated in FIGS. 2 and 3. Thus the hollow core (for instance the passages 10 defined between the ribs 11 of the core and the helix 16) opens into the open end 17 of a cylindrical or other bore 18 which extends through the stub 2 and the cylindrical body of the holder 3.

In the particular embodiment shown in FIG. 2, the holder 3 is mounted in conventional manner in the bore 19 of a hand piece 20 which has a cylindrical head 21 defining the bore 19 and a hand grip 22 and by which the holder is caused to rotate (by means not shown) within the bore 19.

In the embodiment shown in FIG. 2, the bore 18 leads to an annular passage 23 in the cylindrical head 21, and this annular passage leads into a further bore 24 through the hand-piece to means by which material may be sucked through the bores 24 and 18 away from the drilling file, or may be forced through the bores 24 and 18 into the drilling file. Appropriate seals are provided around the annular passage 23 to prevent leakage.

Instead of providing the supply of suction or pressurised fluid through the annular passage 23, it may be provided to the bore 18 through any convenient location. For instance the bore 18 may terminate in a pressure or suction supply at the point marked 25 or at a point at the extreme end of the holder 3, distant from the spring file.

What is claimed is:

1. A dental root canal file (1) which has a drilling end (5) and a holder end (6) interconnected by a shank (7) and wherein the drilling end (5) and the shank (7) have a maximum diameter of not more than 2 mm and are formed of at least one hollow helix (16), and wherein the helix (16) is a substantially closed helix which can flex during drilling rotation and has an external surface (15) which is abrasive to dental root canal material and in which adjacent windings (8a, 8b, 8c) of the helix (16) carry lengthwise spacers (13) whereby adjacent windings are substantially in contact with each other but define openings (14) between the windings.

2. A file according to claim 1 in which there is at least one internal lengthwise passage (10) along the drilling end and the shank towards the holder end for the transfer of material towards the holder end or towards the drilling end.

3. A file according to claim 2 in which the drilling end or the shank, or both, are supported internally by a flexible web (9) fitted within the file.

4. A file according to claim 3 which is tapered to a minimum diameter at the drilling end (5) of 0.1 to 0.4 mm.

5. A file according to claim 4 in which the shank has a maximum diameter which is at least 1.5 times the diameter of the drilling end and is 0.3 to 1.5 mm.

6. A file according to claim 5 and further including a dental tool holder having a stub on which said file is mounted for rotation counter to the direction of twist of the helix of the file.

7. A holder according to claim 6 in which there is at least one internal lengthwise passage (10) along the drilling end and there are means (18) in the holder for transferring material from or to this passage.

8. A file according to claim 1 in which the drilling end or the shank, or both, are supported internally by a flexible web (9) fitted within the file.

9. A file according to claim 8 which is tapered to a minimum diameter at the drilling end (5) of 0.1 to 0.4 mm.

10. A file according to claim 1 which is tapered to a minimum diameter at the drilling end (5) of 0.1 to 0.4 mm.

11. A file according to claim 10 in which the shank has a maximum diameter which is at least 1.5 times the diameter of the drilling end and is 0.3 to 1.5 mm.

12. A file according to claim 1 and further including a dental tool holder having a stub on which said file is mounted for rotation counter to the direction of twist of the helix of the file.

13. A holder according to claim 12 in which there is at least one internal lengthwise passage (10) along the drilling end and there are means (18) in the holder for transferring material from or to this passage.

14. A file according to claim 1 which is formed of at least two hollow helixes which are co-wound and are interconnected substantially in an end to end relationship and wherein each helix (16) is a substantially closed helix which can flex during rotation and has an external surface which is abrasive to dental root canal material.

15. A file according to claim 14 in which the shank has a maximum diameter which is at least 1.5 times the diameter of the drilling end and is 0.3 to 1.5 mm.

16. A file according to claim 14 in which there is at least one internal lengthwise passage (10) along the drilling end and the shank toward the holder end for the transfer of material towards the holder end or towards the drilling end.

17. A file according to claim 14 in which the drilling end or the shank, or both, are supported internally by flexible web (9) fitted within the file.

18. A file according to claim 17 which is tapered to a minimum diameter at the drilling end (5) of 0.1 to 0.4 mm.

19. A file according to claim 14 which is tapered to a minimum diameter at the drilling end (5) of 0.1 to 0.4 mm.

20. A file according to claim 14 and further including a dental holder having a stub on which said file is mounted for rotation counter to the direction of the twist of the helix of the file.

* * * * *